(12) United States Patent
Xie et al.

(10) Patent No.: US 7,344,873 B2
(45) Date of Patent: Mar. 18, 2008

(54) METHODS OF ADENOVIRUS PRODUCTION

(75) Inventors: Liangzhi Xie, North Wales, PA (US); Charles F. Goochee, North Wales, PA (US)

(73) Assignee: Merck & Co., Inc., Rahway, NJ (US)

(*) Notice: Subject to any disclaimer, the term of this patent is extended or adjusted under 35 U.S.C. 154(b) by 407 days.

(21) Appl. No.: 10/509,293

(22) PCT Filed: Mar. 27, 2003

(86) PCT No.: PCT/US03/09269

§ 371 (c)(1),
(2), (4) Date: Sep. 23, 2004

(87) PCT Pub. No.: WO03/085138

PCT Pub. Date: Oct. 16, 2003

(65) Prior Publication Data

US 2005/0176146 A1    Aug. 11, 2005

Related U.S. Application Data

(60) Provisional application No. 60/368,654, filed on Mar. 29, 2002.

(51) Int. Cl.
*C12N 7/00* (2006.01)
*A61K 39/235* (2006.01)

(52) U.S. Cl. .................. 435/235.1; 435/325; 424/233.1

(58) Field of Classification Search ...................... None
See application file for complete search history.

(56) References Cited

U.S. PATENT DOCUMENTS 3,962,424 A     6/1976   Zygraich et al.
5,837,520 A  *  11/1998  Shabram et al. ............. 435/239
5,994,128 A    11/1999   Fallaux et al.

FOREIGN PATENT DOCUMENTS

EP          658626       6/1995
WO     WO 01/02607 A1    1/2001
WO     WO 02/22080 A2    3/2002

OTHER PUBLICATIONS

Cortin et al. Biotechnol. Prog. 2004, 20:858-863.*
Nadeau et al. Biotechnology Advances, 2003, 20:475-489.*
Bett et al., 1994, "An efficient and flexible system for construction of adenovirus vectors with insertions or deletions in early regions 1 an 3", Proc. Natl. Acad. Sci. USA 91:8802-8806.
Capstick et al., 1967, "Factors affecting the production of foot-and-mouth disease virus in deep suspension cultures of BHK21 Clone 13 cells", J.Hyg. 65:273-280.
Fallaux et al., 1996, "Characterization of 911: A New Helper Cell Line for the Titration and Propagation of Early Region 1-Deleted Adenoviral Vectors", Human Gene Therapy 7:215-222.

Fallaux et al., 1998, "New Helper Cells and Matched Early Region 1-Deleted Adenovirus Vectors Prevent Generation of Replication-Competent Adenoviruses", Human Gene Therapy 9:1909-1917.
Gao et al., 2000, "A Cell Line for High-Yield Production of E1-Deleted Adenovirus Vectors without the Emergence of Replication-Competent Virus", Human Gene Therapy 11:213-219.
Hoggan et al., 1959, "The Effect of the Temperature of Incubation on the Formation and Release of Herpes Simplex Virus in Infected FL Cells", Virology 8:508-524.
Imler et al., 1996, "Novel complementation cell lines derived from human lung carcinoma A549 cells support the growth of E1-deleted adenovirus vectors", Gene Therapy 3:75-84.
Jardon et al., 2003, "pH, pCO2, and Temperature Effect on R-Adenovirus Production", Biotechnol. Prog. 19:202-208.
Le Doux et al., 1999, "Kinetics of Retrovirus Production and Decay", Biotechnol. Bioeng. 63:654-662.
McTaggart et al., 2000, "Effects of Culture Parameters on the Production of Retroviral Vectors by a Human Packaging Cell Line", Biotechnol. Prog. 16:859-865.
Parks et al., 1997, "A Helper-Dependent System for Adenovirus Vector Production Helps Define a Lower Limit for Efficient DNA Packaging", J. Virol. 71:3293-3298.
Ross et al., 1979, "The Effects of Temperature and pH variations on Plaque Production by Different Virulence Types of Myxoma Virus", J. Gen. Virol. 43:213-216.
Schiedner et al., 2000, "Eficient Transformation of Primary Human Aminiocytes by E1 Functions of Ad5: Generation of New Cell Lines for Adenoviral Vector Production", Human Gene Therapy 11:2105-2116.
Schweitzer-Thumann et al., 1994, "Effect of an elevated temperature on the replication of HIV1 in a monocytic cell line", Res. Virol. 145:163-170.
Shabram P. W. et al., 1997, "Analytical Anion-Exchange HPLC of Recombinant Type-5 Adenoviral Particles", Human Gene Therapy 8:453-465.

* cited by examiner

*Primary Examiner*—Stacy B. Chen
(74) *Attorney, Agent, or Firm*—Henry P. Wu; Sheldon O. Heber

(57) ABSTRACT

A simple yet effective method of increasing production of a thermo-stable virus, such as adenovirus and picornavirus, is presented. The method entails a temperature shift strategy whereby the culture of host cells are shifted to a sub-optimal temperature for a period of time prior to virus infection or cells are grown at a sub-optimal level for the entire cell expansion process including one or more than one passages of cell growth from cryopreserved cells, followed by a shift back to a more optimal temperature at or near the time of virus infection of the respective host cells. Adaptation of such a temperature shift strategy present a simple yet effective method to substantially increase recoverable virus within a respective host cell/virus production scheme without the need to further manipulate other culture and/or media conditions within an established host cell/virus production scheme.

8 Claims, 10 Drawing Sheets

METHODS OF ADENOVIRUS PRODUCTION

CROSS-REFERENCE TO RELATED APPLICATIONS

This application is the National Stage of International Application PCT/US03/09269, filed Mar. 27, 2003, which claims benefit of priority to U.S. provisional application 60/368,654, filed Mar. 29, 2002.

STATEMENT REGARDING FEDERALLY-SPONSORED R&D

Not Applicable

REFERENCE TO MICROFICHE APPENDIX

Not Applicable

FIELD OF THE INVENTION

The present invention relates to a method of maximizing production of a thermo-stable virus based on a cell culture temperature shift strategy which results in a substantial enhancement of thermal stable virus production. The manipulation of cell culture conditions calls for growing cells at a sub-optimal host cell growth temperature for a period of time prior to virus infection, by shifting the cell growth temperature down to a sub-optimal level for a period of time or by growing cells at a sub-optimal temperature for the entire multiple passages of cell expansion process from the inoculation of a cryopreserved ampule of cells, followed by shifting the temperature up to a higher level prior to, simultaneous to, or after virus infection of the host cells. This methodology results in a substantial increase in recoverable virus as compared with known temperature schemes for virus production within a host cell culture.

BACKGROUND OF THE INVENTION

Advances in the areas of the use of recombinant viral vectors for gene therapy and DNA vaccination applications have created a need for large scale manufacture and purification of clinical-grade virus. One such family of viruses are the adenoviruses. The adenoviruses are grouped within the family Adenoviridae, which are split into the genus *Aviadenovirus* (birds) and *Mastadenovirus* (human, simian, bovine, equine, porcine, ovine, canine and opossum). A review of the family Adenoviridae can be found in Fundamental Biology, 3$^{rd}$ Ed., Fields, B. N., Knipe, D. M., and Howley, P. M., Ed., at Chapter 30, pp. 979-1016 (1996), which is hereby incorporated by reference. Of specific interest in gene vaccination and/or gene therapy applications is the use of a replication incompetent adenovirus, crippled by E1 or further deletions, including "gutless" adenovirus vectors. The adenovirus genome is generally associated with benign pathologies in humans, and the genomic organization of the virus has been well studied since its discovery in the early 1950s. In addition, the genome is amenable to manipulation, depending on the strategy utilized to construct the respective vector. A replication-incompetent virus (such as an E1/E3 deleted Ad5gag vector expressing a HIV gag transgene, as exemplified herein) requires a cell line which complements the deletions. Any such cell line may be used to generate recombinant virus vectors, with preferred, but not limiting, cell lines including 293 cells and PER.C6™ cells. To this end, numerous 1$^{st}$ generation recombinant adenovirus vectors have been described in the literature (e.g., see Bett, et al., 1994, *Proc. Natl. Acad. Sci.* 91:8802-8806; WO 01/02607 and WO 02/22080). "Gutless" adenoviral vectors are a 2$^{nd}$ generation adenoviral vector generally devoid of viral protein-coding sequences, frequently with viral proteins supplemented in trans by a helper virus (often an E1-deleted adenovirus) grown with the helper-dependent (HD) adenovector in a packaging cell line (e.g., PER.C6™). Absent viral proteins, these viral vectors can, in the alternative, be supplemented in trans by a cell line and/or "helper virus" capable of expressing the structural and functional adenoviral proteins necessary for successful replication, packaging and rescue. In view of the increased popularity of these viral vectors and the ultimate need to prepare commercial scale quantities of either a viral vector based vaccine or gene therapy vehicle, it has become essential to develop more efficient qualitative and quantitative methodology for production of commercial grade recombinant adenovirus vectors.

It has been shown that temperature is an important process parameter for both cell growth and virus production. The physiological temperature of 37° C. has been shown to be optimal for growth of a majority of mammalian cell lines. Temperatures below 37° C. historically are shown to reduce cell growth rate, overall cell metabolism, and specific product formation in mammalian cells (see, e.g., Moore, et al., 1997, *Cytotechnology* 23:47-54; Chuppa, et al., 1997, *Biotechnol Bioeng.* 55:328-338). The optimal temperature for virus production depends on the virus strain and the host cell line, but has most often been found to be below 37° C., including 34° C. for herpes simplex virus (HSV) production in FL cell culture (Hoggan and Roizman, 1959, *Virology* 8:508-524), 32 to 34° C. for myxoma virus (Ross and Sanders, 1979, *J. Gen. Virol.* 43:213-216), and 35° C. for foot-and-mouth disease virus in suspension BHK 21 cell cultures (Capstick et al., 1967, *J. Hyg. Camb.* 65:273-280), and 32° C. for cold adapted influenza viruses in MDCK cells. Temperatures above 37° C. are generally not suitable or even non-permissive for virus replication (Schweitzer-Thumann et al., 1994, *Res. Virol.* 145:163-170). For highly heat-labile viruses such as retrovirus, virus productivity can be significantly increased by shifting the culture temperature down from 37° C. (during cell growth) to 32° C. for virus production, primarily due to increased virus stability at a lower temperature (McTaggart and Al-Rubeai, 2000, *Biotechnol. Prog.* 16:859-865).

Despite these reports, there remains a need for the development of a large scale process for virus production from cell culture which address both quantitative and qualitative issues that are imposed upon a commercialized viral-based vaccine and/or gene therapy product. The present invention addresses and meets these needs by disclosing an optimized cell culture and virus production process which defines optimal temperature ranges, resulting in an improved virus productivity as well as elimination of intra-batch productivity variations.

SUMMARY OF THE INVENTION

The present invention relates to a method of maximizing production of a thermo-stable virus based on a cell culture temperature shift strategy which results in a substantial enhancement of thermal stable virus production. The manipulation of temperature within the cell culture/virus production process disclosed herein relies upon a temperature shift strategy whereby (1) the culture of host cells are shifted to a sub-optimal temperature for a period of time prior to virus infection or, (2) the host cell culture is inoculated and grown at a respective sub-optimal temperature, followed by a shift back to a more optimal growth temperature at or near the time of virus infection of the respective host cells. Adaptation of such a temperature shift strategy presents a simple yet effective method to substantially increase recoverable virus within a respective host cell/virus production scheme without the need to further manipulate other culture and/or medium conditions within an established host cell/virus production scheme.

While any virus which is amenable to production in a temperature controlled cell culture environment is envisioned to fall within the scope of this disclosure, the present invention is especially applicable to thermo-stable viruses, such as members of the Adenoviridae family (including all known adenovirus serotypes, and recombinant virus generated from such an adenovirus serotype, including any first or second generation recombinant adenovirus vector known in the art) and members of the Picornavirus family (e.g., poliovirus, rhinovirus, hepatitis A virus, Foot and Mouth Disease Virus). A preferred virus is any serotype of adenovirus, and especially preferred is any recombinant $1^{st}$ or $2^{nd}$ generation recombinant adenovirus vector containing at least one heterologous transgene (see, e.g., e.g., see Bett, et al., 1994, *Proc. Natl. Acad. Sci.* 91:8802-8806; WO 01/02607 and WO 02/22080, the three publications hereby incorporated by reference).

As noted above, the present invention relies in part on a temperature shift strategy for cell growth which comprises reducing the culture temperature to a sub-optimal level for a period of time prior to virus infection or growing cells at a sub-optimal level for the entire cell expansion process including one or more than one passages of cell growth from cryopreserved cells, followed by a shift up to or near the physiological temperature for production of that particular virus prior to, simultaneous to, or after virus infection of the host cells. Various parameters which may be further manipulated in relation to the temperature shift methodology disclosed herein and which fall within the scope of the present invention include but are not necessarily limited to (1) altering the range of the shift to sub-optimal culture conditions; (2) altering the length of time of host cell culture at a sub-optimal temperature; and, (3) coordinating the time of infecting the cell culture with virus with a return to an optimal cell culture condition at or near the known physiological optimum for the respective host cell/virus system, this temperature shift occurring at a reasonable point in time surrounding the time of virus seeding, namely prior to virus infection of the cell culture, simultaneous to virus infection or at a point in time subsequent to virus infection of the cell culture.

One embodiment of the present invention relates to a cell culture temperature shift strategy to enhance virus production; wherein the temperature shift comprises a lowering of the cell culture temperature to a level sub-optimal for cell growth for a period of time prior to infecting the cells with the respective virus, such as a recombinant adenovirus vector. At or near the time of virus infection, the temperature is again shifted to the physiological cell culture temperature, or a temperature which approximates the physiological culture temperature; the combination of cell exposure at the low temperature and the shift upwards reflecting a physiologically optimum practice for virus production.

Another embodiment of the present invention relates to a cell culture temperature shift strategy to enhance virus production; wherein the temperature shift comprises a lowering of the cell culture temperature to a level sub-optimal for cell growth from the time of inoculating the cell culture with host cells from cryopreserved cells and continuing growth of the cell culture at a sub-optimal temperature for one or more than one passages until a temperature shift to an optimal temperature, which should occur at a reasonable point in time surrounding the time of virus seeding, namely prior to virus infection of the cell culture, simultaneous to virus infection or at a point in time subsequent to virus infection of the cell culture.

To this end, the present invention relates to a method of producing virus which comprises inoculating and culturing host cells in an appropriate medium at a temperature below a physiological optimum for host cell growth, infecting the host cells with a virus, resulting in virus-infected host cells, culturing the virus-infected host cells at or near a physiologically optimum temperature for producing virus, harvesting and lysing host cells, and then purifying virus away from the harvested, lysed host cells, resulting in a purified virus product.

A specific embodiment of the present invention relates to a method of producing virus which comprises inoculating and culturing host cells in an appropriate medium at a temperature at or near a physiological optimum for host cell growth, shifting the temperature of the host cell culture to a temperature below a physiological optimum for host cell growth, infecting the host cells with a virus, resulting in virus-infected host cells, culturing the virus-infected host cells at or near a physiologically optimum temperature for producing virus, harvesting and lysing host cells and purifying virus away from the harvested, lysed host cells, which results in a purified virus product.

The time frame for a shift to a suboptimal temperature is preferably from about 4 hours to the entire pre-infection culture period (including from the time of inoculating the culture media with the host cells via inoculation of a cryopreserved ampule of cells) prior to the infection step; including but not limited to an initial culture inoculation at a suboptimal temperature, one to several cell passages at a suboptimal temperature, followed by a temperature shift up to a physiologically optimum temperature for virus infection and production.

The methodology disclosed herein and as summarized in part in the previous paragraphs of this section are preferably applied to any serotype of a $1^{st}$ or $2^{nd}$ generation adenovirus. Preferable pre- and post-infection cell culture temperatures include but are not limited to a range of from about 31° C. to 35° C. for suboptimal cell growth s and from about 35° C. to 38° C. as a physiological optimum range for any culture period before (pre-infection) or after (post-infection) infection of the host cell culture with a virus seed stock.

It is an object of the present invention to provide for a simple yet effective methodology for enhancing virus production in an established host cell/virus production culture system by incorporating a temperature scheme as disclosed herein for cell growth and virus infection.

It is a further object to provide for such improved virus production methodology by incorporating a temperature shift strategy during virus production which calls for a shift to a sub-optimal temperature during cell culture for a period of time prior to seeding the culture with virus, followed by a second temperature change in the culture system which results in a temperature shift back to or near what would be a physiological optimum for the respective host cell/virus production culture system.

DETAILED DESCRIPTION OF THE INVENTION

Figure 1:
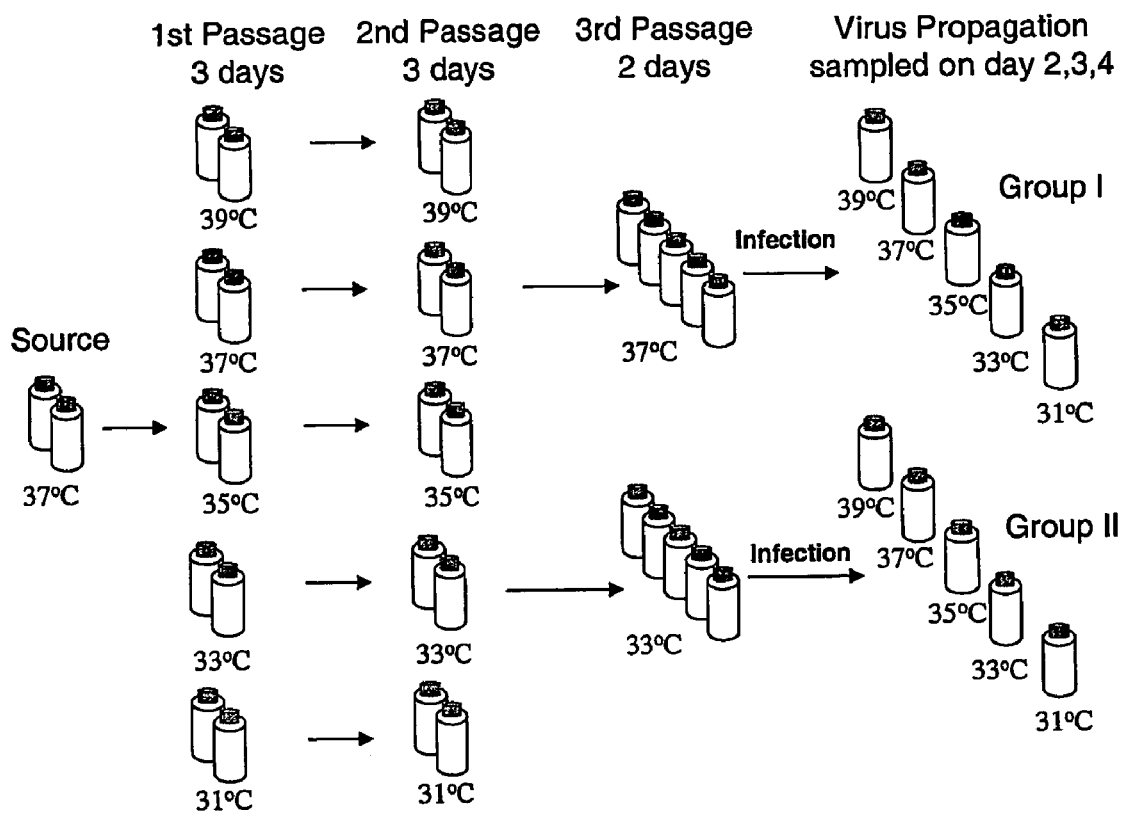
FIG. 1 shows a schematic design of multiple passages of PER.C6™ cells and adenovirus infection at temperatures in roller bottles under serum-free conditions.

The present invention relates to a method of maximizing the production of a virus which is relatively thermo-stable under culture conditions, typically any non-enveloped virus, such as adenoviruses, parvoviruses, reoviruses, and/or picornaviruses. It is an accepted practice that cell growth in culture is typically conducted at the physiological temperature of 37° C. and virus propagation is conducted either at the same temperature as cell growth or shifted downward to a lower temperature. The basis for such a production strategy has been that culture at the physiological temperature allows optimal cell growth but the optimal temperature for the production of many viruses is usually lower due to improved productivity and stability. The present invention is based on a counter intuitive approach involving cell culture/virus production temperature ranges which result in a substantial enhancement of thermal stable virus production. More specifically, the present invention relates to a cell culture/virus production temperature shift strategy whereby culture of host cells are shifted to a sub-optimal culture temperature for a period of time prior to virus infection or cells are grown at a sub-optimal level for the entire cell expansion process including one or more than one passages of cell growth from cryopreserved cells, followed by a shift back to a more optimal temperature for virus production. Production of a recombinant adenovirus serotype 5 encoding a HIV gag transgene (Ad5gag) is exemplified herein. It is shown herein that a 2-3 fold enhancement in recombinant Ad5gag production occurs when the temperature for host cell growth is shifted down to a sub-optimal level for a period of time prior to the virus infection. The temperature is shifted back up to optimal levels post virus infection.

Therefore, the present invention relates to a method of maximizing production of a thermo-stable virus based on a cell culture temperature shift strategy which results in a substantial enhancement of thermal stable virus production. The manipulation of temperature within the cell culture/virus production process disclosed herein relies upon a temperature shift strategy whereby (1) the culture of host cells are shifted to a sub-optimal temperature for a period of time prior to virus infection or, (2) the host cell culture is inoculated and grown at a respective sub-optimal temperature, followed by a shift back to a more optimal growth temperature at or near the time of virus infection of the respective host cells. Adaptation of such a temperature shift strategy presents a simple yet effective method to substantially increase recoverable virus within a respective host cell/virus production scheme without the need to further manipulate other culture and/or media conditions within an established host cell/virus production scheme. While specific cell culture and virus production conditions are disclosed within the Example sections herein, it will be within the purview of the artisan of ordinary skill to utilize this temperature shift strategy to optimize virus production for other thermo-stable viruses, regardless of the respective host cell/virus combination. The artisan may, with the present teachings in hand, adapt and optimize a temperature shift strategy which results in the highest possible increase in virus production. It is also within the scope of the present invention to alter or manipulate culture conditions, media components and other such steps or methods which are known to the artisan which may be used in combination with a temperature shift strategy. Such parameters include but are not limited to altering the range of the shift to sub-optimal culture conditions (e.g., a cell culture shift from 37° C. to 33° C. and back to 37° C. vs. 37° C. to 31° C. and back to 37° C.), the length of time of host cell culture at a sub-optimal temperature (e.g., from the time of inoculation, 1 day, 4 days, 20 days etc.), as well as a coordination of virus infection with a return to an optimal cell culture conditions (e.g., post-infection, at the time of infection, or at a specific time prior to the virus infection). Regardless of the specific parameters adopted, incorporation of a temperature shift strategy will effectively allow for a substantial increase in virus production versus the utilization of those same parameters which omit a temperature shift cell culture strategy. In other words, the temperature shift methodology as disclosed herein will be especially useful in increasing virus production over and above the production levels which exist for a respective host cell/virus system.

In view of the discussion, supra, and the Example sections, infra, the present invention relates to a cell culture temperature shift strategy to enhance virus production; wherein the temperature shift comprises a lowering of the cell culture temperature to a sub-optimal level for a period of time prior to contacting the cells with the respective virus, such as a recombinant adenovirus vector. At or near the time of virus infection, the temperature is again shifted to the physiological cell culture temperature, or a temperature which approximates the physiological culture temperature. As exemplified herein, production of a recombinant adenovirus vector is optimized using a temperature shift strategy. Host cells are grown at the optimal growth temperature range from about 35-38° C., more preferably at about 36-38° C., and especially at 37° C. at early passages to allow rapid expansion of cell numbers for large scale production, which reduces the duration of the batch cycle. The cell growth temperature is then shifted down to a sub-optimal temperature within a range from about 31° C. to about 35° C. (e.g., 33° C.) and maintained for up to several days prior to the virus infection. After the virus infection, the temperature is shifted up to into the 35-38° C. range to maximize the virus productivity. This temperature shift strategy resulted in a significant enhancement (2-3 fold in roller bottles and ca. 2-fold in controlled 2 L stirred tank bioreactors) in volumetric and cell-specific virus productivity as compared to the traditional approaches of maintaining the same temperature or shifting the temperature down post the virus infection. While the present invention is exemplified for a recombinant adenovirus 5 serotype, the temperature shift strategy disclosed herein is applicable to other adenovirus serotypes, as well as other thermostable viruses, such as picornaviruses. The invention is especially related to the increased production of all adenovirus serotypes using E1-transformed mammalian cell lines (293, PER.C6, etc.) in all types of culture vessels (T-flasks, roller bottles, Nunc Cell Factories, Cell Cubes, Wave bioreactor, spinner flask, shaker flask, stirred tank bioreactors, etc.) where temperature control is implemented. Therefore, as noted above, the present invention relies in part on a temperature shift strategy for cell growth which comprises reducing the culture temperature to a sub-optimal level for a period of time prior to virus seeding, followed by a return to or near the physiological temperature for production of that particular virus prior to, simultaneous to, or after virus infection of host cells. Various parameters which may be further manipulated in relation to the temperature shift methodology disclosed herein and which fall within the scope of the present invention include but are not necessarily limited to (1) altering the range of the shift to sub-optimal culture conditions; (2) altering the length of time of host cell culture at a sub-optimal temperature; and (3) coordinating the time of infecting the cell culture with virus with a return to an optimal cell culture condition at or near the known physiological optimum for the respective host cell/virus system, this temperature shift occurring at a reasonable point in time surrounding the time of virus seeding, namely prior to virus infection of the cell culture, simultaneous to virus infection or at a point in time subsequent to virus infection of the cell culture.

In an embodiment of the present invention, the cell growth temperature is first shifted from an optimal physiological temperature (e.g., from about 35° C. to about 38° C.) to a temperature at or below 35° C. for a period of time and then returned to culture at a physiologically optimal temperature at or near the time of virus infection of the cell culture. This regime results in an effective increase in virus production upon infection and return to culture conditions at optimal levels. Any "suboptimal" temperature at or below 35° C. is contemplated (with ranges from 31° C. to 35° C., preferably 31° C. to 34° C., and most preferably from about 31° C. to about 33° C., with a higher range of 33° C. to 35° C. still being useful to the artisan) to practice the invention, as long as the "suboptimal" cell growth temperature supports reasonable cell growth and the optimal temperature for cell culture growth is from about 35° C. to about 38° C. (again, with about 36-38° C. and then 36.5 to 37° C. representing especially preferred ranges) and as long as there is an increase of temperature from the cell growth to virus infection. As noted above, while a lower sub-optimal temperature may easily be tested by the artisan, a preferred sub-optimal temperature range is from 31° C. to 35° C., with a more preferred range from 31° C. to 34° C., with sub-ranges of 31° C. to 33° C. and/or 33° C. to 35° C. being useful to the artisan. A preferable temperature shift strategy is one which effectively minimizes duration of cell expansion from a vial to large productions scale: cells are expanded at the physiological temperature of 37° C. and shifted to the sub-optimal temperature for a specific time, usually for at least 24 hours prior to the virus infection, with a return to the temperature of cell growth (such as 37° C.) or slightly lower, depending upon the respective host cell and/or virus).

As noted in the previous paragraph, an embodiment of the present invention relates to the period of time which the culture is subjected to sub-optimal growth conditions. The time period can range anywhere from several hours, to several passages (multiple days), to entire cell expansion period inoculating the initial culture from a frozen vial containing a stock of host cells. Included in the scope of the present invention is a scenario, and all in between, whereby the culture is initially inoculated at the sub-optimal temperature and kept at this lower temperature until seeding with the virus stock. It should also be understood that minor manipulations from a sub-optimal temperature regime (e.g., such as a short term increase in temperature followed by a downward shift back to the "sub-optimal" temperature) and the length of the sub-optimal growth, and the time of returning the temperature back to the optimal temperature with respect to the time of virus infection (e.g., increase the temperature several hours after the virus infection or several hours before the infection, etc) is well within the scope of the present invention.

The host cell for use in the temperature shift protocol comprising the present invention may be any mammalian cell line which supports replication of the respective thermostable virus, especially any host cell line known in the art which will support infection and replication of a $1^{st}$ or $2^{nd}$ generation adenovirus vector. A preferred host cell is a host cell line which supports infection and replication of an E1 and/or and E1/E3 deleted recombinant adenovirus. As disclosed herein, such a replication-incompetent virus (such an Ad5gag, as exemplified herein) requires a helper cell line which complements the Ad5 E1 deletion. Any such cell line may be used to generate recombinant virus, with preferred, but not limiting, cell lines including 293 cells, PER.C6™ cells, 911 cells from a human embryonic retinal cell line (Fallaux et al. 1996, *Human Gene Therapy* 7: 215-222); E1-transformed amniocytes (Schiedner et al. 2000, *Human Gene Therapy* 11:2105-2116); an E1-transformed A549 cell line for a human lung carcinoma (Imler et al. 1996, *Gene Therapy* 3:75-84) and GH329: HeLa (Gao et al. 2000, *Human Gene Therapy* 11: 213-219). Such a cell line is transformed to support replication and packaging of a respective recombinant adenovirus, such as an E1 or E1/E3 deleted recombinant adenovirus. Additional cell lines which may be utilized in the present invention are again cell lines which have been adapted to act as host cells for a particular thermo-stable virus. It is preferable that the cell line be a continuous cell line and more preferable that the source of the cultured cells originate from a non-neoplastic tissue. It is also preferable that the source be mammalian, most likely from a primate origin, and especially of human origin. Again, a preferred cell line is a cell line which is useful for the propagation of an Ad E1 or E1/E3 deleted recombinant virus; a recombinant virus which compliment E1-deleted adenovirus vector included cell lines transfected with the gene encoding Ad E1 which have been selected for this transformed phenotype, such as 293 cells (epithelial cells from human kidney) and PER.C6™ (human embryonic retinoblasts). Other cell types include but are not limited to HeLa cells, A549 cells, KB cells, CKT1 cells, NIH/sT3 cells, Vero cells, Chinese Hamster Ovary (CHO) cells, or any eukaryotic cells which support the adenovirus life cycle.

It is preferred, but not necessary, that the culture be a suspension culture; a suspension culture which is maintained in a suitable medium which supports cell growth, virus infection and virus production. Such a suspension culture is well known in the art and, again, may be modified in any number of ways known to the artisan without effecting a useful incorporation of a temperature shift strategy to increase virus production. The culture medium can be subjected to various growth conditions which are suitable for virus production, including but not limited to batch, fed-batch or continuous perfusion operations to introduce fresh medium into the culture medium. Again, the culture medium can be any suitable medium for maintaining, the cells and permitting the propagation of the respective virus. Numerous examples of media suitable for use in the practice of the present invention, and the principles to generate modified or new suitable media, are widely known in the art. For a review, see Chapter 8 (serum-based media) and Chapter 9 (serum-free media) from *Culture of Animal Cells: A Manual of Basic Technique*; Ed. Freshen, R I, 2000, Wiley-Lisps, pp. 89-104 and 105-120, respectively. In general, either serum-based or serum free media will be manipulated to enhance growth of the respective cell line in culture, with a potential for inclusion of any of the following: a selection of secreted cellular proteins, diffusable nutrients, amino acids, organic and inorganic salts, vitamins, trace metals, sugars, and lipids as well as perhaps other compounds such as growth promoting substances (e.g., cytokines). As seen with the Trade Index at pp. 483-515 of *Culture of Animal Cells: A Manual of Basic Technique*, (id.), the potential suppliers of both information and cell culture media are virtually endless. A preferable medium used in the context of the present invention is a defined medium, such as the medium exemplified herein as Ex-Cell 525 medium (from JRH Biosciences, [http//www.jhrbio.com]) and 293 SFM II medium (from Invitrogen). It is also desirable that such media are supplemented with glutamine, as disclosed herein.

The virus types which are amenable to the temperature shift strategy of the present invention are preferably from two virus families that are non-enveloped DNA virus that infect human cells. These two virus types are the Adenoviridae family (including all known adenovirus serotypes, and recombinant virus generated from such an adenovirus serotype) and members of the Picornavirus family (e.g., poliovirus, rhinovirus, hepatitis A virus, Foot and Mouth Disease Virus). An adenovirus 5 serotype, a member of the Adenoviridae family, is exemplified herein. The term "virus" as used herein is meant to cover any virus which is amenable to completing its replication cycle in the mammalian cell line of choice. Therefore, this term is certainly meant to include wild type virus, any genetically modified virus such as an attenuated virus, or more likely a recombinant virus vector which may be a development candidate for a potential gene therapy and/or DNA vaccination application. Such programs have created a need for large scale manufacture and purification of clinical-grade virus. A preferred recombinant virus which is amenable to the improved cell culture/virus production parameters disclosed herein are a family of viruses known as the adenoviruses. The adenoviruses are grouped within the family Adenoviridae, which are split into the genus *Aviadenovirus* (birds) and *Mastadenovirus* (human, simian, bovine, equine, porcine, ovine, canine and opossum). Adenovirus are well known in the art and are subject to many reviews, such as can be found in Fundamental Biology, $3^{rd}$ Ed., Fields, B. N., Knipe, D. M., and Howley, P. M., Ed., at Chapter 30, pp. 979-1016 (1996), which is hereby incorporated by reference. Of specific interest in gene vaccination and/or gene therapy applications is the use of a first generation replication incompetent adenovirus, crippled by E1 and/or E3 gene deletions, based on any of a number of adenovirus serotypes, such as serotype 5 of adenovirus. An additional type of vector is referred to as a $2^{nd}$ generation adenovirus vector, and commonly includes a class of adenovirus vectors including "gutless" adenovirus vectors. Gutless adenoviral vectors are adenoviral vectors generally devoid of viral protein-coding sequences, frequently with viral proteins supplemented in trans by a helper virus (often an E1-deleted adenovirus) grown with the HD adenovector in a packaging cell line (e.g., PER.C6™). Absent viral proteins these viral vectors can, in the alternative, be supplemented in trans by a cell line capable of expressing the structural and functional adenoviral proteins necessary for successful replication, packaging and rescue. The only cis elements generally present on the HD vector are the packaging signal and the inverted terminal repeats (ITRs). Preferably, inclusive of transgene and any exogenous non-transcribed nucleic acid incorporated therein (stuffer DNA), the Ad virion is roughly at least 75% of the wild-type genome length. The Ad virion has been reported to essentially exhibit a lower packaging limit of approximately 75% of the wild-type genome length; see Parks & Graham, 1997 *J. Virology* 71(4):3293-3298. Adenoviral vector genomes smaller than 27.7 kb were found to package inefficiently and frequently undergo rearrangement. Adenovirus has a broad cell tropism including professional antigen presenting cells such as macrophages and dendritic cells, can infect (if not replicate in) cells from most animal species, and can be produced in large quantities in appropriate human cell lines designed to provide the E1 gene product in trans.

Figure 2A:
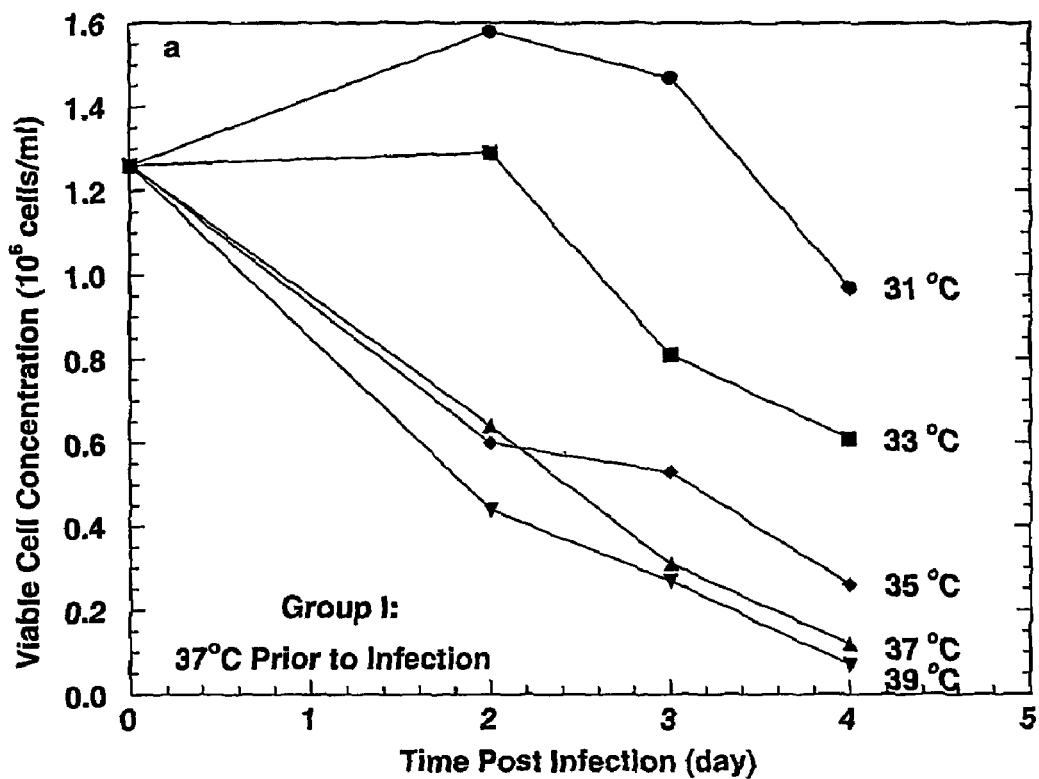
FIG. 2A and FIG. 2B show viable cell concentrations of adenovirus infected PER.C6™ cells cultivated at temperatures of 31, 33, 35, 37, and 39° C.: A. Group I with cells grown at 37° C. prior to virus infection; B. Group II with cells grown at 33° C. for 8 days prior to virus infection.
Figure 2B:
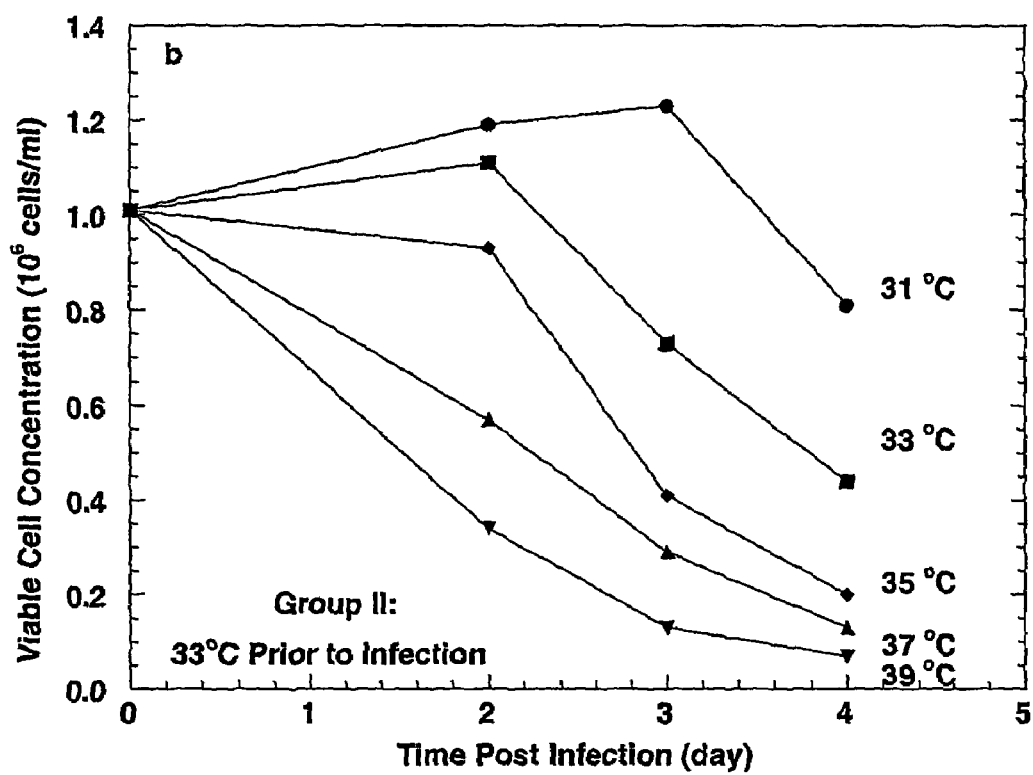
Figure 3A:
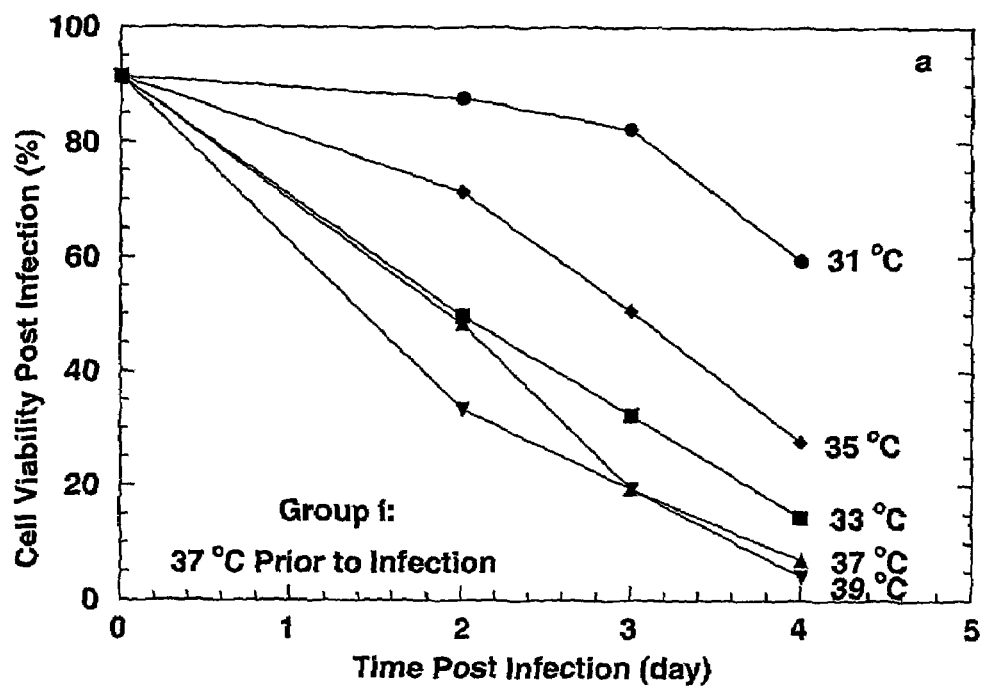
FIGS. 3A and 3B show viabilities of adenovirus infected PER.C6™ cells cultivated in at temperatures of 31, 33, 35, 37, and 39° C.: A. Group I with cells grown at 37° C. prior to virus infection; B. Group II with cells grown at 33° C. for 8 days prior to virus infection.
Figure 3B:
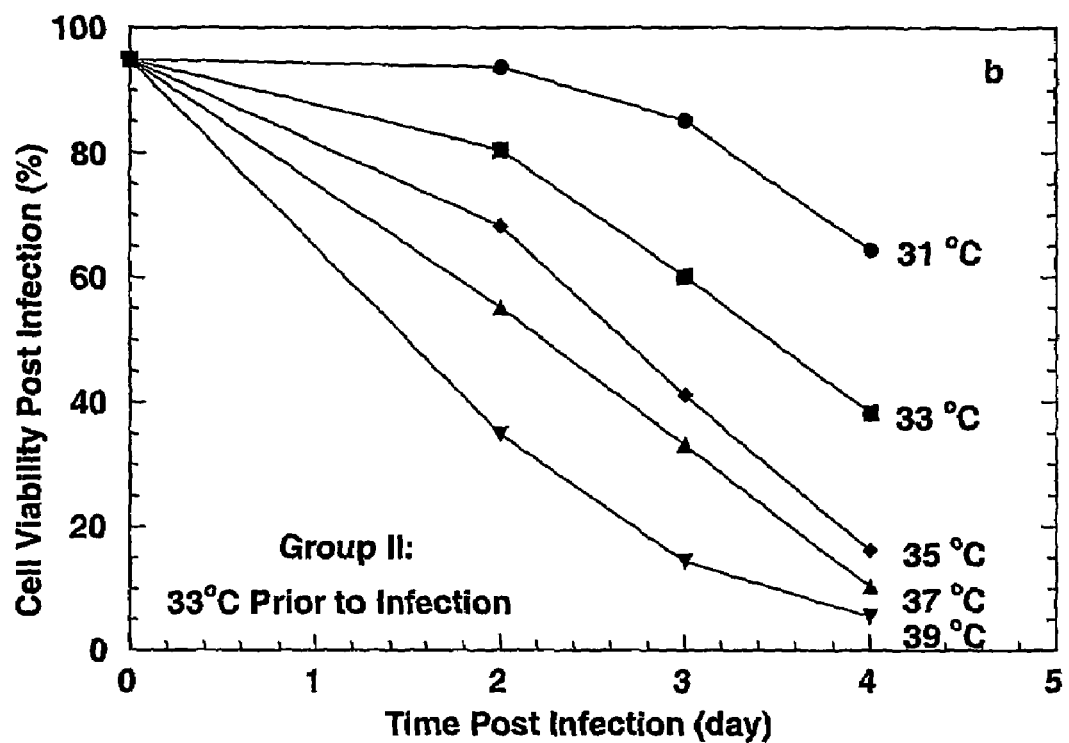

In a series of experiments which effectively exemplify the present invention, but in no way suggest a limitation to the scope thereof, PER.C6™ cells grown at 33 and 37° C. were infected with a first generation adenovirus vector expressing HIV-1 gag at temperatures of 31, 33, 35, 37, and 39° C. for virus production. The effects of temperature on the infected cell metabolism and adenovirus production were studied. It was observed that PER.C6™ cell growth became much more sensitive to culture temperature post adenovirus infection (FIGS. 2A and 2B in Example 1). Even at low temperatures, PER.C6 cells still grew well, albeit at a lower rate and maintained high viability at low temperatures. As a result of the virus infection and rapid replication at high temperatures, cell growth was arrested and cell viability decreased rapidly as a result of the virus infection and rapid replication (FIGS. 3A and 3B in Example 1). Temperature also affected the adenovirus replication kinetics and productivity. The physiological temperature of 37° C. supported the fastest virus replication, regardless of the cell growth temperature prior to infection. Peak virus concentration occurred earlier at higher temperatures. With cells grown at 37° C. prior to infection, the highest intracellular virus concentration occurred at 35° C. It occurred at 37° C. with cells grown at 33° C. prior to infection. Cell expansion history prior to virus infection was shown to play a critical role in infected cell metabolism and virus production. Cells grown at 33° C. prior to infection had significantly higher (60% to 200%) virus productivity at all temperatures post infection. The results demonstrate that culture temperature is a highly critical process parameter in adenovirus production. The temperature shift improvement has been exemplified in both small scale roller bottle and 2 L stirred tank or vessel bioreactor studies. As shown herein, again as an example but in no way a limitation, the cell growth rate at a temperature below 35° C. is significantly reduced but this suboptimal temperature for cell growth prior to virus infection is optimal for subsequent virus production at a higher temperature (i.e., an upward temperature shift). It is also shown herein that one to two passages of cell growth at such a suboptimal temperature is suited well for adenovirus vector production. The temperature shift strategy disclosed herein can be easily implemented at any production scale by controlling temperature at different levels during the process. At large scale production, it is perceived that cell growth temperature during early cell expansion prior to the cell growth and virus infection in the large scale production can be set at the optimal physical temperature to achieve the fastest cell expansion for reduction of batch cell duration. However, the inventors have shown that a downward shift in temperature during pre-infection cell culture (e.g., such as seven to sixteen days prior to the planned virus infection), the temperature for cell growth can be shifted down to 31-35° C., more preferably from 31° C. to 34° C., with sub-ranges of 31° C. to 33° C. and/or 33° C. to 35° C. remaining very useful, depending upon the respective cell culture conditions (this could occur in the seeding vessel for the final production vessel and the final production vessel). Immediately after the virus infection, the temperature is shifted up to 35-38° C., preferably from 36-38° C. and most preferably from 36-37° C. to achieve optimal virus production, as exemplified in the following non-limiting examples. These non-limiting Examples are presented to better illustrate the invention.

EXAMPLE 1

Ad5HIV-1 gag Production in PER.C™ Cells

Materials and Methods:

Cell Line and Maintenance—PER.C6™ cells (Fallaux et al., 1998, *Human Gene Therapy* 9:1909-1917, see also U.S. Pat. No. 5,994,128), a human embryonic retinoblast cell line licensed from Crucell (Leiden, The Netherlands), were derived by transfecting human embryonic retinoblast cells with an adenovirus type 5 E1 gene using a phosphoglycer-atekinase promoter. The E1 gene expression confers immortalization on the cells and allows retention of the E1(+) genotype in the absence of a selective marker. The cells were adapted to suspension culture, and routinely maintained in EX-Cell™ 525 serum-free medium (JRH Biosciences, Lenexa Kans.) supplemented with 4 mM L-glutamine (Mediatech Inc., Herndon Va.), in roller bottles at 37° C. and 5% $CO_2$/95% air overlay.

Growth of Cells at Various Temperatures—Two roller bottles of PER.C6™ cells maintained at 37° C. were pooled and used to plant ten 850 $cm^2$ roller bottles (Corning, Cambridge, Mass.) at $4\times10^5$ viable cells per ml and 200 ml working volume per roller bottle in Ex-Cell™ 525 serum-free medium supplemented with 4 mM L-glutamine. The bottles were gassed with 5% $CO_2$/95% air and divided randomly into five groups of two bottles each and incubated for 3 days with a rotation rate of 4 RPM at nominal temperatures of 31, 33, 35, 37, and 39° C. At the end of the 3-day incubation, the two roller bottles from each temperature groups were pooled to plant two new roller bottles and incubated at the respective temperatures for a second 3-day passage. The cells from the 33 and 37° C. groups were selected to passage a third time in 5 roller bottles per group for two days, followed by virus infection (See FIG. 1). The two groups of five roller bottles derived from cells grown at 37 and 33° C. prior to the infection are designated as Group I and II, respectively.

Virus Seed Stock—A first generation adenovirus type 5 vector (E1 and E3 deleted) expressing the p55 gag transgene from HIV-1 (see WO 01/02607), was amplified in PER.C6™ cells.

Viral Infection at Various Temperatures—The 5 roller bottles from the 37° C. and 33° C. groups were infected on day 2 post planting. The spent medium was removed by centrifugation, followed by resuspending the cell pellets in fresh EX-Cell 525™ medium supplemented with 4 mM glutamine. A fixed quantity of the virus stock was added to infect each roller bottle, resulting in a multiplicity of infection (MOI) of ~240 viral particles (VP) per cell. The 5 infected bottles from each group were then incubated at nominal temperatures of 31, 33, 35, 37, and 39° C. Samples were taken from each roller bottle at 2, 3 and 4 days post virus infection, and centrifuged to clarify. Aliquots of supernatant were removed and stored at −70° C. for assay of extracellular virus. The cell pellets were resuspended in fresh medium to yield a 10-fold concentration from the original culture, followed by 3 times freeze and thaw. The resulting lysates were then clarified by centrifugation and stored at −70° C. prior to assay for intracellular virus concentrations.

Temperature Monitoring and Control—Controlled-temperature cultivation took place in water-jacketed incubators (Forma Scientific, Marietta Ohio) and a 37° C. warm room (Environmental Specialties, Raleigh N.C.). Nine days prior to commencement of the experiment, the incubators and warm room were adjusted to their target temperature setpoints. Temperature mappings of the incubators and warm room were carried out during this period to confirm stability of temperature control. Six bottle positions were defined on roller apparatus in each of the incubators and the warm room. Temperature probes were inserted through holes in the roller bottle caps, with the bottles in place and rotating during measurement. These measures ensured the accuracy of the culture temperature for the study.

Analytical Methods—Cell concentrations were measured with a hemocytometer and viability was assessed by trypan blue exclusion. Viral particle (VP) concentrations were measured by anion exchange HPLC (AEX assay), using a technique adapted from Shabram et al. (1997, *Human Gene Therapy* 8:453-465). The coefficient of variation for the anion exchange HPLC assay is typically less than 10%. A quantitative PCR based potency assay was employed to estimate the virus infectivity. Virus samples were used to infect 293 monolayer cultures in 96 wells. The viral DNA was extracted from each well at 24 hours post infection and quantified by a PCR method. Virus infectivity was estimated from a standard virus stock titered by the traditional $TCID_{50}$ assay.

Calculation Methods—The time integral of viable cell concentration was calculated by multiplying the average cell concentration with the culture time between two time points. Specific virus productivity was calculated by dividing the virus concentration by the viable cell concentration at infection.

Figure 4A:
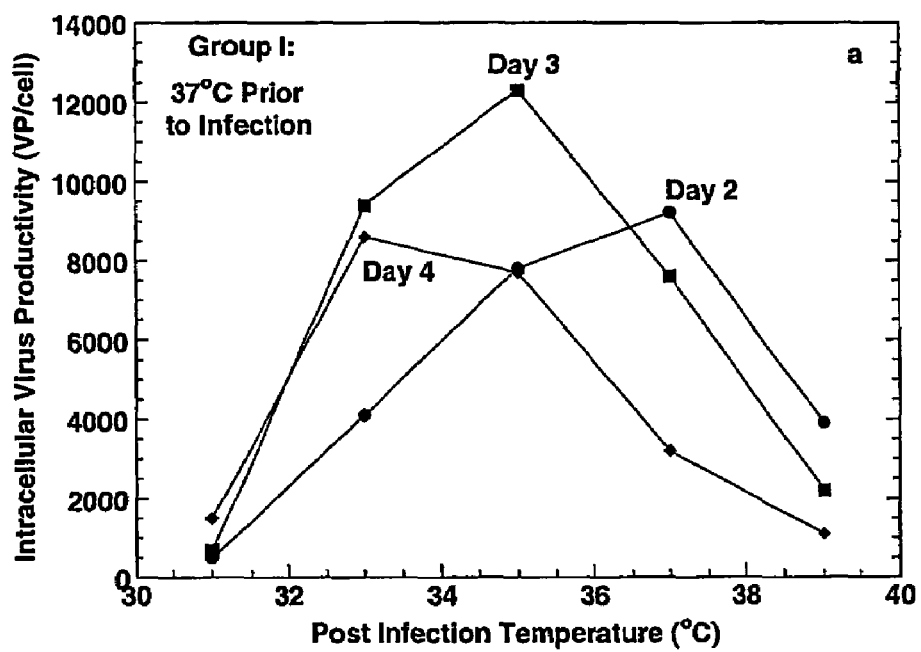
FIGS. 4A, 4B and 4C shows adenovirus replication kinetics and effects of culture temperature on virus productivity in PER.C6™ cultures at temperatures of 31, 33, 35, 37, and 39° C.: A. intracellular virus productivity in Group I with cells grown at 37° C. prior to virus infection; B. intracellular virus productivity in Group II with cells grown at 33° C. for 8 days prior to virus infection; C. virus productivity ratio of Group II to Group I.
Figure 4B:
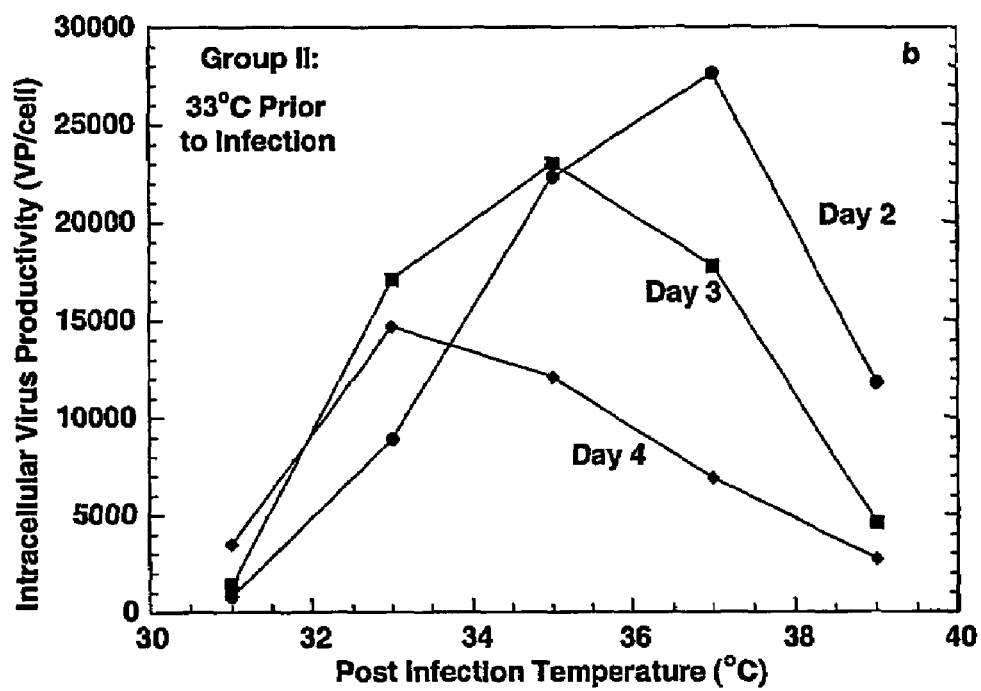
Figure 4C:
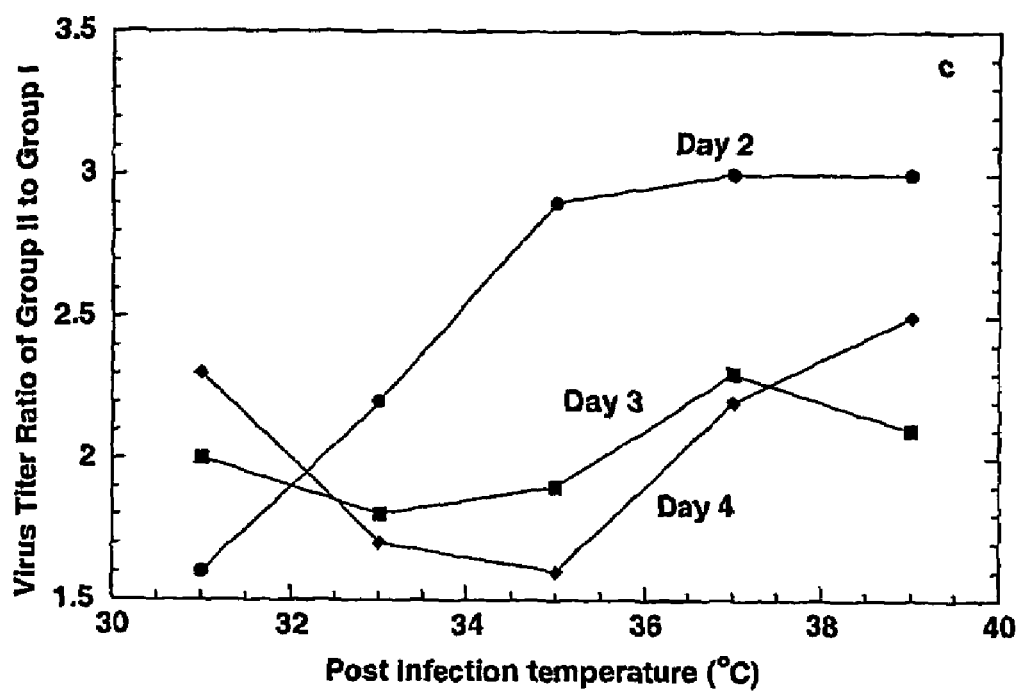

Results:

Effects of Temperature on Virus Productivity—All roller bottles were sampled on day 2, 3, and 4 post virus infection for virus concentration measurements. In previous experience, virus concentration at day 1 post infection was shown to be below the detection limit of the AEX assay and hence no sample was taken on day 1 post infection in an effort to avoid a reduction in the culture volume from the roller bottles. The samples were concentrated roughly 10-fold by centrifuging down the cells and resuspending the infected cell pellets in a smaller volume of culture medium. Virus particle concentrations in the cell pellets were measured by HPLC assay after a 3× freeze/thaw process for virus release. The virus particle concentrations in the cell pellets were normalized on a per cell basis as shown in FIG. 4 (FIG. 4A—Group I; FIG. 4B—Group II). In Group I, the highest virus concentration in the cell pellets occurred at 37° C. on day 2 post infection, suggesting that the virus replication rate was the highest at this temperature. Deviation to either side of this optimal temperature resulted in slower virus replication. However, intracellular virus concentration measured from the cell pellets seemed to have peaked earlier at higher temperatures. On day 3 post infection, virus concentration in the cell pellets decreased at both 37 and 39° C. The reduced concentration was presumably a result of release of intracellular virions into the culture medium as cell viability decreased rapidly and cell lysis occurred. Although the virus replicated slightly slower at 35° C., virus concentration continued to rise on day 3 post infection, exceeding the peak concentration reached at 37° C. a day earlier. The highest intracellular virus concentration on day 4 was shifted further down to 33° C. At 31° C., the intracellular virus concentration was only a fraction of those at higher temperatures, although it continued to rise on day 4. However, it was unlikely to reach a significantly higher level due to the poor replication kinetics.

In Group II, the maximum intracellular virus concentration occurred at 37° C. on day 2, at 35° C. on day 3, and at 33° C. on day 4, which is exactly the same as Group I. Peak intracellular concentration occurred on day 2 at 37 to 39° C., on day 3 at 33 to 35° C., and on day 4 at 31° C., which is also the same as Group I. However, there are major differences between the two groups. First, the highest intracellular virus concentration occurred at 37° C. on day 2 in Group II versus 35° C. on day 3 in Group I. Second, virus productivity was significantly higher in Group II across all temperatures. A head-to-head comparison is shown in FIG. 6C where the virus titer ratios of Group II to Group I on the same day are plotted for all five different temperatures. On day 2 post infection, virus titers in Group II were 60% to 200% higher than in Group I. The differences were significantly larger at high temperatures. Differences between the two groups became smaller on day 3 and 4 but remained significant.

The virus concentrations in the supernatants were usually below the detection limit of the HPLC assay. Hence, a more sensitive infectivity assay was employed to measure this virus. Supernatant and cell pellet samples were measured head-to-head in the same assay in order to estimate the relative distribution of intracellular and extracellular viruses. As expected, a significant amount of virus was released into the culture medium, especially at the late stage of virus replication when the cell viability was significantly reduced. These data confirmed the assumption that the reduction in the virus concentration measured in the cell pellets was primarily due to the virus release into the culture medium. Although the above discussion on the virus productivity was based on measurements in cell pellets only, the same general picture was obtained when the percentages of virus in the supernatants were accounted for.

The effects of culture temperature on the adenovirus infection of PER.C6™ cells were thoroughly investigated. Profound differences in infected cell growth and virus production were observed. Cells infected with the same MOI but incubated at different temperature post infection resulted in different growth behavior. At high temperatures (35-39° C.), the adenovirus infection resulted in complete cell growth arrest, but significant cell growth post infection was observed at lower temperatures (31-33° C.) (FIG. 2A for Group I and FIG. 2B for Group II). Cell viability post infection also showed a strong dependency on the culture temperature (FIG. 3A for Group I and FIG. 3B for Group II). It decreased rapidly over the course of virus replication at higher temperatures but maintained at reasonably high levels at lower temperatures. The MOI used for infection should be high enough for a synchronized infection. The limited cytopathic effect at lower temperatures indicates slow and impaired virus replication, which is consistent with low virus concentrations measured over four days post infection.

Temperature also affected adenovirus replication rate dramatically. The virus was found to replicate faster at high temperatures, with the optimal temperature at 37° C. As a result, virus concentration in cell pellet peaked earlier at 37-39° C. than at 31-35° C. However, the optimal kinetic temperature did not coincide with the maximum virus productivity. Cells grown at 37° C. prior to the infection produced the highest virus concentration at 35° C. while cells grown at 33° C. prior to infection produced the highest at 37° C.

A strong correlation between virus release into culture medium and cell viability was observed. This correlation provides a simple and rapid estimate of virus percentage in the medium, which could be employed to develop harvest strategies, especially in cases where only intracellular virus can be harvested. Cell growth history was found to have significant impact on cell growth, metabolism, and virus productivity. In addition, there were significant differences in the adenovirus replication kinetics and productivity. Cells grown at 33° C. prior to infection had 60% to 200% higher productivities at all temperatures.

EXAMPLE 2

Effect of Passage Time at Sub-Optimal Temperature on Virus Production

Figure 5:
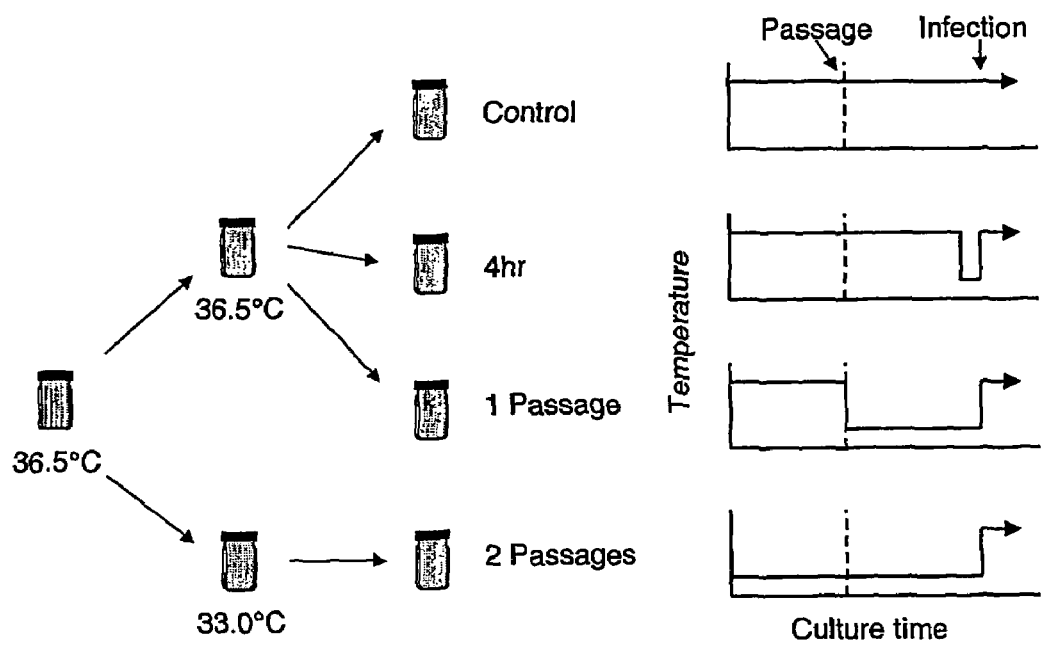
FIG. 5 shows the experimental design with similarities to that in FIG. 1, namely to measure the effect of the length of time at a "sub-optimal" temperature has on Ad5gag virus production.

Materials and Methods are essentially as described in Example 1. Briefly, FIG. 5 summarizes the experimental design. Two bioreactors were inoculated with PER.C6® cells in 293 SFM II (Invitrogen, Grand Island, N.Y.) serum-free medium supplemented with 6 mM L-glutamine (Biowhittaker Inc., Walkersville, Md.) at 33.0 and 36.5° C. Cells were grown to ~2.5×10$^6$ cells/ml and diluted in new bioreactors at the appropriate temperature. The temperature control scheme for each vessel is depicted in FIG. 5, using 33.0° C. "temperature shifts" ranging from 2 passages to 4 hours. The cells were infected with a replication-defective adenovirus encoding a HIV-1 gag transgene using a multiplicity of infection of 70 viral particles per viable cell. The temperature of all reactors was changed to 36.5° C. immediately after infection. Viral concentration at 48 hours post infection (hpi) from supernatant and Triton-X100 lysed whole broth samples (TL) containing both intracellular and extracellular virus was determined from HPLC assay daily. The virus bulk was then harvested by addition of a cell lysis buffer to release the remaining intracellular virus into the supernatant or by releasing intracellular virus using mechanical shear. The resulted whole broth virus bulk was then further purified through multiple steps for the removal of cellular debris, host cell proteins and DNA, unpacked viral proteins and DNA, and other impurities. This example reiterates the results presented in Example 1, namely that studies in both roller bottles and 2 L bioreactors indicate that controlling the temperature at 33.0° C. during cell growth (for two passages) and at 37.0° C. during infection enhanced virus production. Cell growth at 33.0° C. is slower (doubling time ~50 hr) than at 36.5° C. (doubling time ~30 hr). This results in an increase in total batch time from ~12 days in bioreactors to ~17 days, which lowers the time-specific virus production of a factory. It will be incumbent upon the skilled artisan to optimize the respective system such that optimal virus production is generated from a "sub-optimal" temperature passage while maintaining the enhanced virus production seen in previous experiments.

Figure 6:
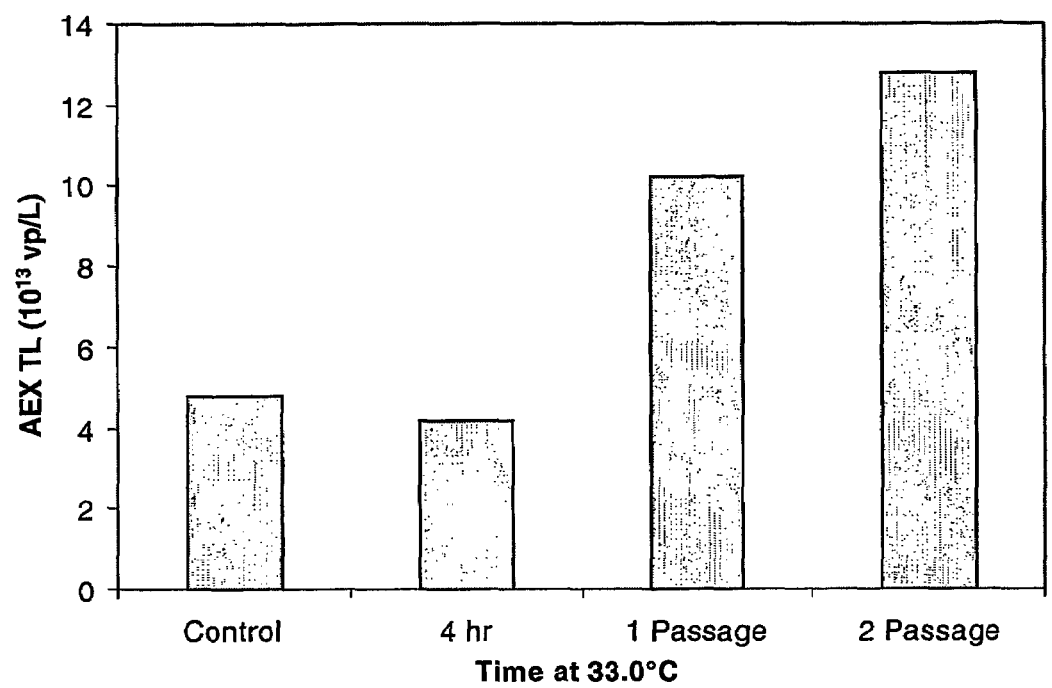
FIG. 6 shows virus production under different temperature schemes from the study described in FIG. 5.

FIG. 6 shows virus production under different temperature control schemes, namely differing time periods at a sub-optimal temperature prior to virus seeding and raising the culture temperature back to a physiological optimum. These data show that a temperature shift of a few hours does not provide optimal enhancement of the virus productivity. The length of the "sub-optimal cell growth" at a reduced temperature can be further optimized to minimize the length of the production process. The data are consistent with the results obtained in roller bottles as described in Example 1. A 2-3 fold enhancement in virus productivity is obtained with the temperature shift strategy for sub-optimal incubation times ranging from 7 to 16 days as compared to the 36.5° C. control. It will be recognized that these data may be reflective of peculiarities of the particular experiment, and that a skilled artisan might optimize culture conditions aside from temperature so as to shorten the sub-optimal incubation time needed for optimal virus growth from the range shown here and to adjusting the time for the temperature shift-up relative to the virus infection time.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method of producing adenovirus, comprising:
   a) culturing host cells at a temperature from 31° C. to 34° C.;
   b) infecting the host cells with an adenovirus, resulting in adenovirus-infected host cells;
   c) culturing the adenovirus-infected host cells at a temperature from 35° C. to 38° C.;
   d) harvesting adenovirus and/or cells containing adenovirus from the culture; and,
   e) purifying adenovirus away from host cell and culture contaminants, resulting in a purified adenovirus product.

2. A method of producing adenovirus, comprising:
   a) inoculating and culturing host cells in an appropriate medium at a temperature from 35° C. to 38° C.;
   b) shifting the temperature of the host cell culture of step a) to a temperature from 31° C. to 34° C.;
   c) infecting the host cells of step b) with a adenovirus, resulting in adenovirus-infected host cells;
   d) culturing the adenovirus-infected host cells at a temperature from 35° C. to 38° C.;
   e) harvesting adenovirus and/or cells containing adenovirus from the culture; and,
   f) purifying adenovirus away from host cell and culture contaminants, resulting in a purified adenovirus product.

3. A method according to claim 2 wherein the culture temperature in step b) is lowered to a temperature from 31° C. to 34° C. for up to the entire cell passages prior to infecting the host cells with the adenovirus.

4. A method according to claim 2 wherein the culture temperature in step b) is lowered to a temperature from 31° C. to 34° C. for at least 24 hours prior to infecting the host cells with the adenovirus.

5. A method according to claim 3 wherein the temperature for cell growth in step a) is from 36° C. to 38° C.

6. A method according to claim 4 wherein the temperature for cell growth in step a) is from 36° C. to 38° C.

7. A method according to claim 3 wherein the temperature for cell growth in step a) is from 36° C. to 38° C. and the temperature for growth of infected host cells of step c) is from 36° C. to 38° C.

8. A method according to claim 4 wherein the temperature for cell growth in step a) is from 36° C. to 38° C. and the temperature for growth of infected host cells of step c) is from 36° C. to 38° C.

* * * * *